Figure 1:
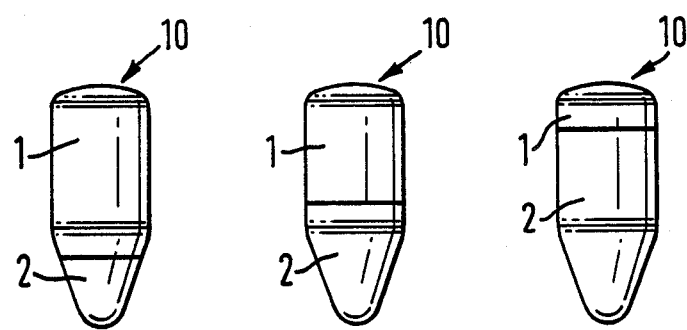

United States Patent [19]

Plevnik et al.

[11] Patent Number: 4,895,363
[45] Date of Patent: Jan. 23, 1990

[54] SET OF PARTS AND METHODS FOR TESTING AND/OR STRENGTHENING PELVIC FLOOR MUSCLES

[76] Inventors: Stanislav Plevnik, Na Grivi 20, Dragomer, Brezovica pri Ljubljani, Ljubljana, Yugoslavia; Marko Stular, Bratov Ucakar 90, 61000 Ljublijana, Yugoslavia

[21] Appl. No.: 239,027

[22] Filed: Aug. 30, 1988

Related U.S. Application Data

[63] Continuation of Ser. No. 849,393, Apr. 8, 1986, abandoned.

[30] Foreign Application Priority Data

Apr. 9, 1985 [GB] United Kingdom ................ 8509008

[51] Int. Cl.$^4$ ............................................ A63B 21/06
[52] U.S. Cl. ........................................ 272/93; 600/29
[58] Field of Search .................. 272/67, 68, 93, 125, 272/119, 122, 123; 128/31, 79, 67, 127, 341, 778; 273/171; 600/29, 3

[56] References Cited

U.S. PATENT DOCUMENTS

| | | | |
|---|---|---|---|
| 1,291,465 | 1/1919 | Foreman | 272/119 |
| 2,763,265 | 9/1956 | Waters | 128/67 |
| 3,838,853 | 10/1974 | Fredenhagen | 272/67 |
| 4,241,912 | 12/1980 | Mercer et al. | 272/125 |
| 4,253,660 | 3/1981 | Tiktin | 272/119 |
| 4,369,967 | 1/1983 | Kimura | 272/119 |
| 4,384,714 | 5/1983 | Kimura | 272/119 |

FOREIGN PATENT DOCUMENTS 2058571 4/1981 United Kingdom ................ 272/93

OTHER PUBLICATIONS

Epidemiology of Micturition Disorders by Thelma M. Thomas, Clinical Gynecologic Urology, The C. V. Mosby Company, (1984).
New Method for Testing and Strengthening of Pelvic Floor Muscles by Stanislav Plevnik, International Continence Society, 15th Annual Meeting, (1985).
Cones: A Conservative Method of Treating Genuine Stress Incontinence by S. Stanton, S. Plevnik, A. Peattie, Third Joint Meeting, International Continence Society and Uro Dynamics Society, (Sep. 1986).
Graded Exercises for the Pelvic Floor Muscles in the Treatment of Urinary Incontinence by J. Laycock, Bradford Royal Infirmary, (Jul. 1987).
Vaginal Cones: A Conservative Method of Treating Genuine Stress Incontinence by A. B. Peattie, S. Plevnik and S. L. Stanton, (Jun. 1987).
Peattie A. B., Plevnik S., Stanton, Vaginal Cones: A Conservative Method of Treating Genuine Stress Incontinence, British Journal of Obstetrics and Gynecology, 95: 1049-1053.
Preattie A. B., Plevnik S., Cones Versus Physiotherapy as Conservative Management of Genuine Stress Incontinence, Proceedings of the 18th Annual Meeting of the International Continence Society, Oslo, pp. 265-266, 1988.
Bridges N., Denning J., Olah K. S., Farrar D. J., A Prospective Trial Comparing Interferential Therapy and Treatment Using Cones in Patients with Symptoms of Stress Incontinence, Proceedings of the 18th Annual Meeting of the International Continence Society, Oslo, pp. 267-268, 1988.
Zanollo A., Vaginal Cones: A New Method to Treat Stress Urinary Incontinence, Proceedings of the 2nd National Congress of the Italian Urodynamic Society, Rome, pp. 39-43, 1988.

*Primary Examiner*—Stephen R. Crow
*Attorney, Agent, or Firm*—Lalos & Keegan

[57] ABSTRACT

A plurality of devices (10) each have identical size and shape, but are of graded weights. A device is inserted into the vagina of a subject, and if the pelvic floor muscles (12) are capable of retaining that weight, the device is replaced by a heavier one. The heaviest that can be retained is a measure of a pelvic floor muscle strength, and the muscles can be exercised by retaining the device for a predetermined time, such as 15 to 20 minutes per day.

7 Claims, 1 Drawing Sheet

SET OF PARTS AND METHODS FOR TESTING AND/OR STRENGTHENING PELVIC FLOOR MUSCLES

This is a continuation of application Ser. No. 06/849,393 filed Apr. 8, 1986, now abandoned.

The present invention relates to a set of parts and methods for testing and/or strengthening pelvic floor muscles.

Exercises for pelvic floor muscles (PFM) as usually prescribed by physicians have certain limitations; women can have difficulty in experiencing the pelvic floor muscle action and they have no information as to how strong the muscles actually are.

To overcome this deficiency, different "perineometer" devices based on biofeedback principles have been developed, and used with the aim of ensuring more efficient and reliable exercising by giving the woman information on proper contraction of the PFM. A typical device of this type consists of a vaginal probe connected to an external unit which provides either audio or visual feedback of any changes in vaginal pressure.

GB No. 2058571 describes a device for exercising the perineal muscles which comprises a shaft having a tapered portion with an enlarged spherical end for insertion in the vagina and provision for suspending various weights from the other end of the shaft.

U.S. Pat. No. 4241912 describes an isometric vaginal exercise device comprising a rounded shaft having a flange at one end thereof. The shaft has a concave portion adjacent the flange, wherein the diameter of the concave portion decreases to a minimum value and then increases to a maximum value with increasing distance from the flange. The concave portion allows gripping of the device by perivaginal muscles of the user. The flange is oval to permit accommodation between the legs of the user. A handle is attached to the flange end of the device.

The main disadvantages of the above techniques are:

(i) Exercising of the PFM may not be reliable, especially when using a perineometer. At rest and during exercises, the vigina is exposed not only to contractions of the pelvic floor but also to any changes in abdominal pressure. This allows for the possibility that, during exercising with a perineometer, the subject will have a similar chance of exercising either only PFM or only abdominal muscles or both, the reading on the perineometer not distinguishing between these alternatives.

(ii) The devices are somewhat complicated in design as well as inconvenient for the subject's use.

From a first aspect, the present invention provides a set of parts for testing and/or strengthening pelvic floor muscles, comprising a plurality of devices each having a substantially identical size and shape such that each device can be inserted into the vagina of a subject, the devices being of different weights such that for a given subject, the pelvic floor muscles will be capable of supporting a said device up to a particular weight. Each of the devices generally approximates to a solid of revolution and may preferably include a right cylindrical portion and a generally conical portion ending in a rounded tip. In order to prepare a set of devices with substantially identical size and shape, each device may conveniently be formed from two or more materials having different densities. By varying the proportion of each material in the devices, a set can be produced having different weights but the same size and shape. Conveniently, a combination of a plastics material such as polymethylmethacrylate or nylon with a metal such as brass or stainless steel may be used to form the devices. Preferably, the devices are formed with a polymethylmethacrylate portion bonded to a brass portion, the size of each portion being selected to give the desired weight to the device. Using these materials we have found it possible to produce devices having an advantageous combination of weight, size and shape. The brass portion is generally provided with a physiologically acceptable coating e.g. by chromium plating.

From a second aspect, the present invention provides a method of testing pelvic floor muscles utilising a plurality of devices of different weights but having identical sizes and shapes and being capable of insertion into the vagina of a subject, the method comprising:

inserting one of the devices and checking whether the pelvic floor muscles can support the device;

if so, replacing the device with a heavier device, and if not, replacing the device with a lighter device; and repeating the above steps until one of the devices is just capable of being supported, the weight of that device providing an indication of the pelvic floor muscle strength.

The present invention also provides a method of exercising pelvic floor muscles based on the above determination of the weight which is just supported when voluntary holding is exerted, the device having that weight being retained by the subject for a predetermined time.

Preferred aspects of the invention provide a biofeedback technique for testing and reliable exercising of the pelvic floor muscles.

Figure 2:
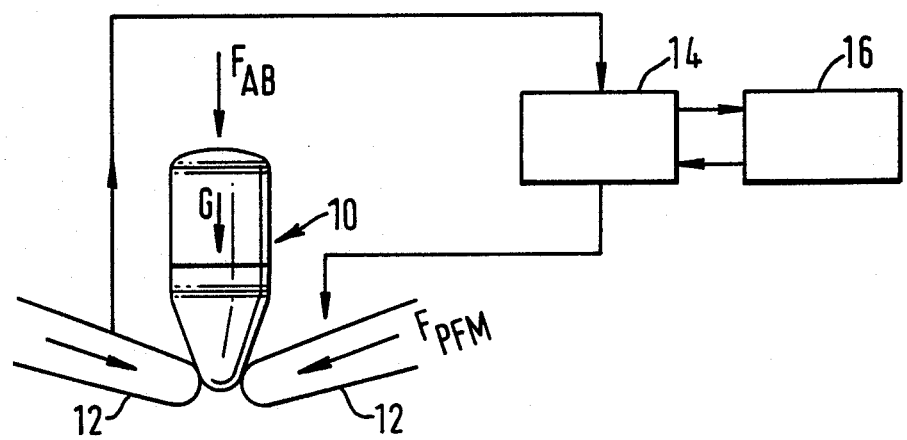

The invention will now be described, by way of example, with reference to the accompanying drawings in which FIG. 1 schematically shows a set of devices according to the invention; and FIG. 2 schematically illustrates a preferred technique of the invention.

The set shown in FIG. 1 comprises three devices or "cones" 10, but in practice a set will conveniently contain nine or more such cones. The cones 10 are of identical size and shape for insertion into the vagina of a subject but each is of different weight. To achieve different weights, the cones are formed of two materials 1 and 2 in varying proportions between the cones.

AS indicated above, the preferred method of the invention employs a set of nine devices or "cones" (each as shown in FIGS. 1 and 2 referenced 10) of equal shape and volume but different weights gradually increasing from cone to cone in the range from 20 to 100 gm. When the cone of the appropriate weight is inserted into the vagina it tends to slip out. This feeling of "losing the cone" provides a powerful sensory biofeedback which makes the pelvic floor contact around the cone, thus retaining it. This path is shown schematically in FIG. 2 as including the pelvic floor muscles 12, the sacral cord 14 and the central nervous system 16. As seen in FIG. 2, the device is generally inserted into the vagina with the tapered end of the device directed outwardly.

10 Normal parous women, aged from 29 to 49 years, were subjected to testing and exercising with the method of the invention.

The cones were successively inserted into the vagina in the standing position. The heaviest cone that could be retained in the vagina while standing and during walking without voluntary holding was taken to be a measure of the resting PFM strength. The heaviest cone that could be retained in the vagina during standing and walking for 1 minute during voluntary holding was taken to be the measure of the active pelvic floor muscle strength.

The cone which could still be comfortably retained by voluntary holding (this is usually the cone which is one step heavier than the cone representing the resting PFM strength) was given to the subject for exercising. The subjects were instructed that the cone would try to slip out of vagina and that they should try to prevent that by contracting the muscles. 15 to 20 minutes were prescribed per day, to be performed during walking or standing at home, for a period of two weeks.

The preliminary results of testing and exercising are shown in the Table below. 14 Days of exercising revealed considerable increase of PFM strength in all subjects.

TABLE

| No of subject | | 1 | 2 | 3 | 4 | 5 | 6 | 7 | 8 | 9 | 10 |
|---|---|---|---|---|---|---|---|---|---|---|---|
| Resting strength (gr) | before exercises | 50 | 40 | 60 | 70 | 50 | 60 | 40 | 60 | 40 | 70 |
| | after exercises | 60 | 50 | 70 | 80 | 60 | 70 | 50 | 60 | 50 | 70 |
| Active strength (gr) | before exercises | 70 | 60 | 70 | 80 | 70 | 70 | 60 | 70 | 60 | 80 |
| | after exercises | 90 | 80 | 80 | 90 | 80 | 80 | 70 | 80 | 80 | 90 |

The new method ensures reliable exercising of PFM. The sensory biofeedback provided by the feeling of "losing the cone" always makes the pelvic floor contract during retaining the cone. The possible increase of abdominal pressure will demand even stronger pelvic floor contraction in order to retain the cone. It is expected that these exercises will prove useful in the treatment of incontinence.

The cone 10 is shown as including a right cylindrical portion and a generally conical portion ending in a rounded tip. Other shapes may be suitable but should have symmetry about a longitudinal axis so as to approximate a solid of revolution. It may be possible to utilise a facetal construction rather than a curved one, but in that case, a relatively large number of facets should be provided to approximate to the preferably rounded shape.

We claim:

1. A method of testing pelvic floor muscles utilizing a set of parts comprising a plurality of exercise devices each having a substantially identical size and shape and having a fixed volume such that each of said devices can be fully inserted into the vagina of a human subject, each of said exercise devices in said set having a weight different from each of the other exercise devices in said set, the method comprising:
    fully inserting one of the devices and checking whether the pelvic floor muscles can support the device;
    if so, replacing the device with a heavier device, and if not, replacing the device with a lighter device; and
    repeating the above steps until one of the devices is just capable of being supported, the weight of that device providing an indication of the pelvic floor muscle strength.

2. A method according to claim 1, wherein the resting strength of the pelvic floor muscles is determined by the subject not exerting voluntary holding.

3. A method according to claim 1, wherein the active strength of the pelvic floor muscles is determined by the subject exerting voluntary holding.

4. A method of exercising pelvic floor muscles utilizing a set of parts comprising a plurality of exercise devices each having a substantially identical size and shape and having a fixed volume such that each of said devices can be fully inserted into the vagina of a human subject, each of said exercise devices in said set having a weight different from each of the other exercise devices in said set, the method comprising:
    fully inserting one of the devices and checking whether the pelvic floor muscles can support the device;
    if so, replacing the device with a heavier device, and if not, replacing the device with a lighter device; and
    repeating the above steps until one of the devices is just capable of being supported, the weight of that device providing an indication of the pelvic floor muscle strength, and
    retaining the device whose weight is just capable of being supported by exerting voluntary holding for a predetermined time.

5. A method according to claim 4, wherein the predetermined time is 15-20 minutes.

6. A method of testing pelvic floor muscles utilizing a set of parts comprising a plurality of exercise devices each having a substantially identical size and shape and having a fixed volume such that each of said devices can be fully inserted into the vagina of a human subject, each of said exercise devices in said set having a weight different from each of the other exercise devices in said set, each of said devices being formed from the least two materials having different densities, the proportion of each material being varied between devices in said set, the method comprising:
    fully inserting one of the devices and checking whether the pelvic floor muscles can support the device;
    if so, replacing the device with a heavier device, and if not, replacing the device with a lighter device; and
    repeating the above steps until one of the devices is just capable of being supported, the weight of that device providing an indication of the pelvic floor muscle strength.

7. A method of exercising pelvic floor muscles utilizing a set of parts comprising a plurality of exercise devices each having a substantially identical size and shape and having a fixed volume such that each of said devices can be fully inserted into the vagina of a human subject, each of said exercise devices in said set having a weight different from each of the other exercise devices in said set, each of said devices being formed from at least two materials having different densities, the proportion of each material being varied between devices in said set, the method comprising:
    fully inserting one of the devices and checking whether the pelvic floor muscles can support the device;
    if so, replacing the device with a heavier device, and if not, replacing the device with a lighter device; and
    repeating the above steps until one of the devices is just capable of being supported, the weight of that device providing an indication of the pelvic floor muscle strength, and
    retaining the device whose weight is just capable of being supported by exerting voluntary holding for a predetermined time.

* * * * *